United States Patent
Huttner et al.

[19]

[11] Patent Number: 6,042,599
[45] Date of Patent: Mar. 28, 2000

[54] TISSUE APPROXIMATION FORCEPS

[75] Inventors: James J. Huttner; David I. Kinsel, both of Sylvania, Ohio

[73] Assignee: Bionix Development Corp., Toledo, Ohio

[21] Appl. No.: 08/967,971

[22] Filed: Nov. 12, 1997

[51] Int. Cl.$^7$ .................................................. A61B 17/28
[52] U.S. Cl. ...................... 606/205; 606/210; 606/208; 606/216
[58] Field of Search ................................... 606/205, 206, 606/207, 208, 210, 216, 151; 294/99.1, 99.2; 433/3

[56] References Cited

U.S. PATENT DOCUMENTS

| | | | |
|---|---|---|---|
| 3,611,842 | 10/1971 | Skipper | 294/99.2 |
| 4,212,305 | 7/1980 | Lahay . | |
| 5,156,431 | 10/1992 | Lowe | 294/99.2 |
| 5,514,148 | 5/1996 | Smith, III | 606/151 |
| 5,611,794 | 3/1997 | Sauer et al. | 606/8 |
| 5,622,492 | 4/1997 | Eli | 433/3 |
| 5,752,973 | 5/1998 | Kieturakis | 606/207 |

OTHER PUBLICATIONS

Approximation forceps, documentation printed from the internet, unknown author and date, 1 page.

How good are tissue adhesives in repairing lacerations?, Harold K. Simon, MD, Mar. 1997, Contemporary Pediatrics, vol. 14, No. 11, pp. 90–96.

Appearance Scales to Measure Cosmetic Outcomes of Healed Lacerations, J.V. Quinn, MD, CCFP (EM), A.E. Drzewiecki, MD, FRCSC, I.G. Stiell, MC, FRCPC, T.J. Elmslie, MD, CCFP, FRCPC, Mar. 1995, The American Journal of Emergency Medicine, vol. 13, No. 2, pp. 229–231.

Long–Term Appearance of Lacerations Repaired Using a Tissue Adhesive, Harold K. Simon, MD; David J. McLario, DO, MS; Thomas B. Bruns, MD; William T. Zempsky, MD; Robert J. Wood, MD; and Kevin M. Sullivan, PhD, MPH, MHA, Feb. 1997, Pediatrics, vol. 99, No. 2, pp. 193–195.

Laceration Repair Using a Tissue Adhesive in a Children's Emergency Department, Thomas B. Bruns, MD; Harold K. Simon, MD; David J. McLario, DO, MS; Kevin M. Sullivan, PhD, MPH, MHA; Robert J. Wood, MD; and K.J.S. Anand, MBBS, DPhil, Oct. 1996, Pediatrics, vol. 98, No. 4, pp. 673–675.

Use of Tissue Adhesives in the Repair of Lacerations in Children, S. Mizrahi, A. Bickel and E. Ben–Layish, Apr. 1988, Journal of Pediatric Surgery, vol. 23, No. 4, pp. 312–313.

Use of cyanoacrylate tissue adhesive for closing facial lacerations in children, David P. Watson, Oct. 21, 1989, British Medical Journal, vol. 299, No. 6706, p. 1014.

A Randomized, Controlled Trial Comparing a Tissue Adhesive With Suturing in the Repair of Pediatric Facial Lacerations, JV Quinn, MD, CCFP (EM, A Drzewiecki, MD, FRCSC, MM Li, MD, FRCPC, IG Stiell, MD, FRCPC, T Sutcliffe, BA, RN, T J Elmslie, MD, CCFP, FRCPC and WE Wood, MD, CCFP, Jul. 1993, Annals of Emergency Medicine, pp. 1130–1135.

(List continued on next page.)

*Primary Examiner*—Michael Buiz
*Assistant Examiner*—(Jackie) Tan-uyen T. Ho
*Attorney, Agent, or Firm*—Emch, Schaffer, Schaub & Porcello Co., L.P.A.

[57] ABSTRACT

The invention comprises tissue approximation forceps which are particularly useful in approximating wound edges where tissue glue is to be used. A handle includes two leg members which mount grip members having grip surfaces. When the handle is squeezed, moving the grip members toward one another, the edges of the wound are moved together without everting. The tissue glue is then applied.

13 Claims, 3 Drawing Sheets

OTHER PUBLICATIONS

Histotoxicity of Cyanoacrylate Tissue Adhesives, Dean M. Toriumi, MD; Wasim F. Raslan, MD; Michael Friedman, MD; and M. Eugene Tardy, MD, May 1990, Archives of Otolaryngology—Head & Neck Surgery, vol. 116, No. 5, pp. 546–550.

Histoacryl—Its Use in Aesthetic Facial Plastic Surgery, Frank M. Kamar, MD and John H. Joseph, MD, Feb. 1989, Archives of Otolaryngology—Head & Neck Surgery, vol. 115, No. 2, pp. 193–197.

A Randomized Trial Comparing Octylcyanoacrylate Tissue Adhesive and Sutures in the Management of Lacerations, James Quinn, MD, George Wells, PhD, Terri Sutcliffe, BScN; Mario Jarmuske, MD; Jennifer Maw, MD, Ian Stiell, MD; and Peter Johns, MD, May 21, 1997, The Journal of the American Medical Assoication, vol. 277, No. 19, pp. 1527–1530.

Cyanoacrylate Tissue Adhesives—An Advance in Wound Care, Alexander T. Trott, MD, May 21, 1997, The Journal of the American Medical Association, vol. 277, No. 19, pp. 1559–1560.

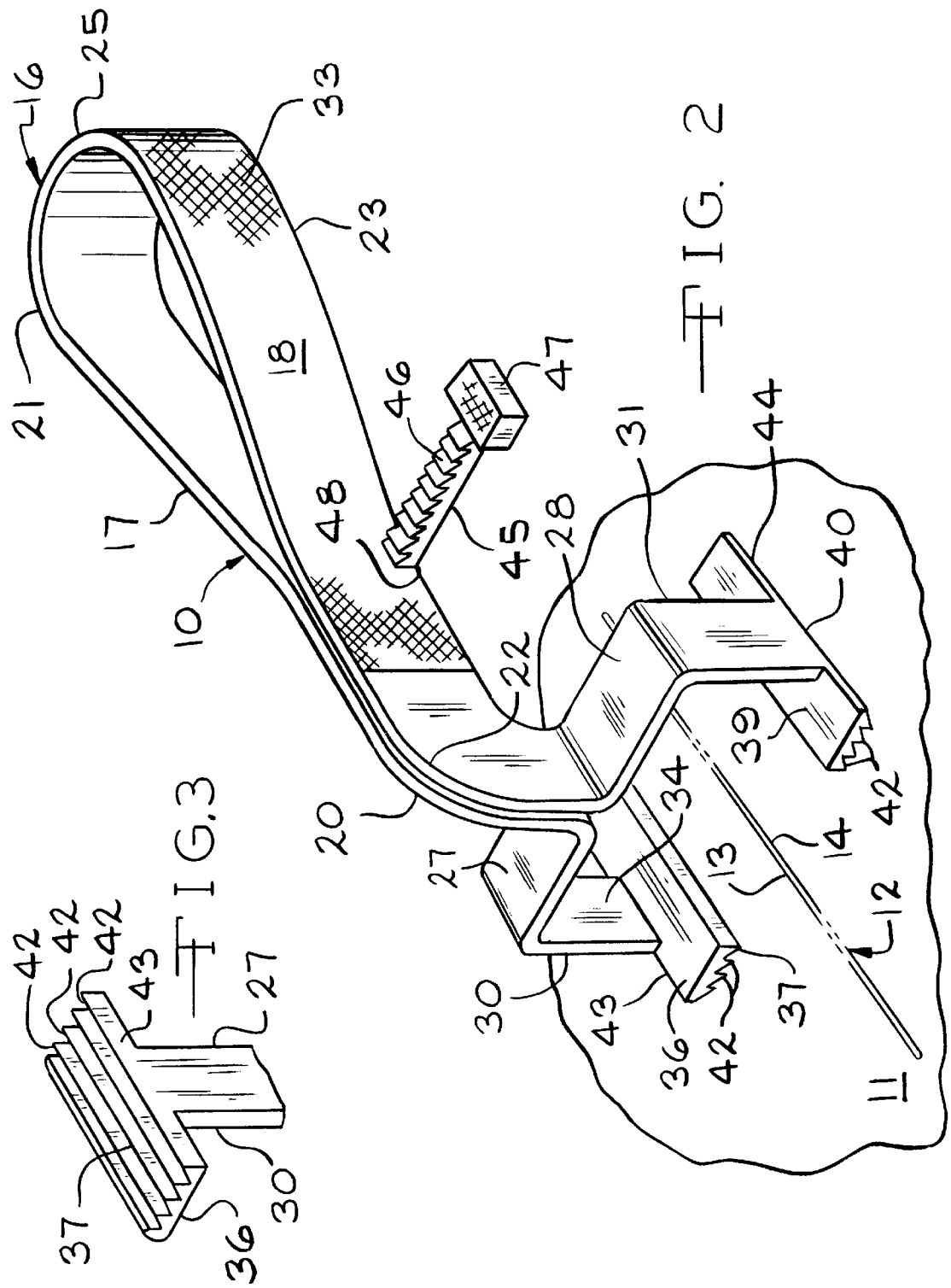

TISSUE APPROXIMATION FORCEPS

BACKGROUND OF THE INVENTION

The present invention is directed to tissue approximation forceps and particularly to forceps which close a wound without everting the wound edges prior to closure.

Prior art tissue forceps have many types of mating handle surfaces, including rat-tooth surfaces, serrated surfaces and cross-hatched surfaces, all for the purpose of grasping the tissue adjacent the edges of a wound in a secure manner. With many prior art forceps, the forceps indent the skin and evert the wound edges during closure. This is often desirable for suturing a wound because the edges eventually flatten and give a cosmetically acceptable result. When prior art tissue forceps are utilized and the wound edges are everted, a satisfactory result does not occur when a tissue glue is utilized rather than suturing. Tissue glues are relatively non-tissue toxic. However, their greatest toxicity occurs when they come into contact with subcutaneous tissue. When the wound edges are everted by prior art tissue forceps, more of the subcutaneous tissue of the wound is exposed which increases the toxic effect of the tissue glue.

Other types of prior art clamps including a clamp for approximating tissue sections are shown in U.S. Pat. Nos. 5,514,148 and 5,611,794.

The tissue approximation forceps, according to the present invention, have surfaces which engage the skin adjacent a wound in a manner which approximates the tissue edges without everting the wound edges.

SUMMARY OF THE INVENTION

The present invention is directed to improved tissue approximation forceps. A handle has a pair of handle members. Each of the handle members has a first and a second end. An end member joins together the second ends of the handle members. A pair of leg members extend outwardly from the first ends of the pair of handle members. Preferably the legs have offsets which define a large viewing area when the forceps are closed. A grip member is mounted by each of the handle members. The grip members have grip surfaces which do not lie in parallel contacting planes. When the handle members are moved together, the grip members and the grip surface are moved toward each other to approximate the separated skin edges.

BRIEF DESCRIPTION OF THE DRAWINGS

FIG. 2 is a view, similar to FIG. 1, showing the tissue approximation forceps in a compressed position;

FIG. 3 is a fragmentary perspective view showing the grip surface of one of the grip members, of the FIG. 1 and FIG. 2 embodiment;

FIG. 4 is a perspective view of another embodiment of tissue approximation forceps, according to the present embodiment in a compressed position; and FIG. 5 is a front elevational view of the FIG. 4 embodiment in the uncompressed position.

DETAILED DESCRIPTION OF THE PREFERRED EMBODIMENTS

Figure 1:
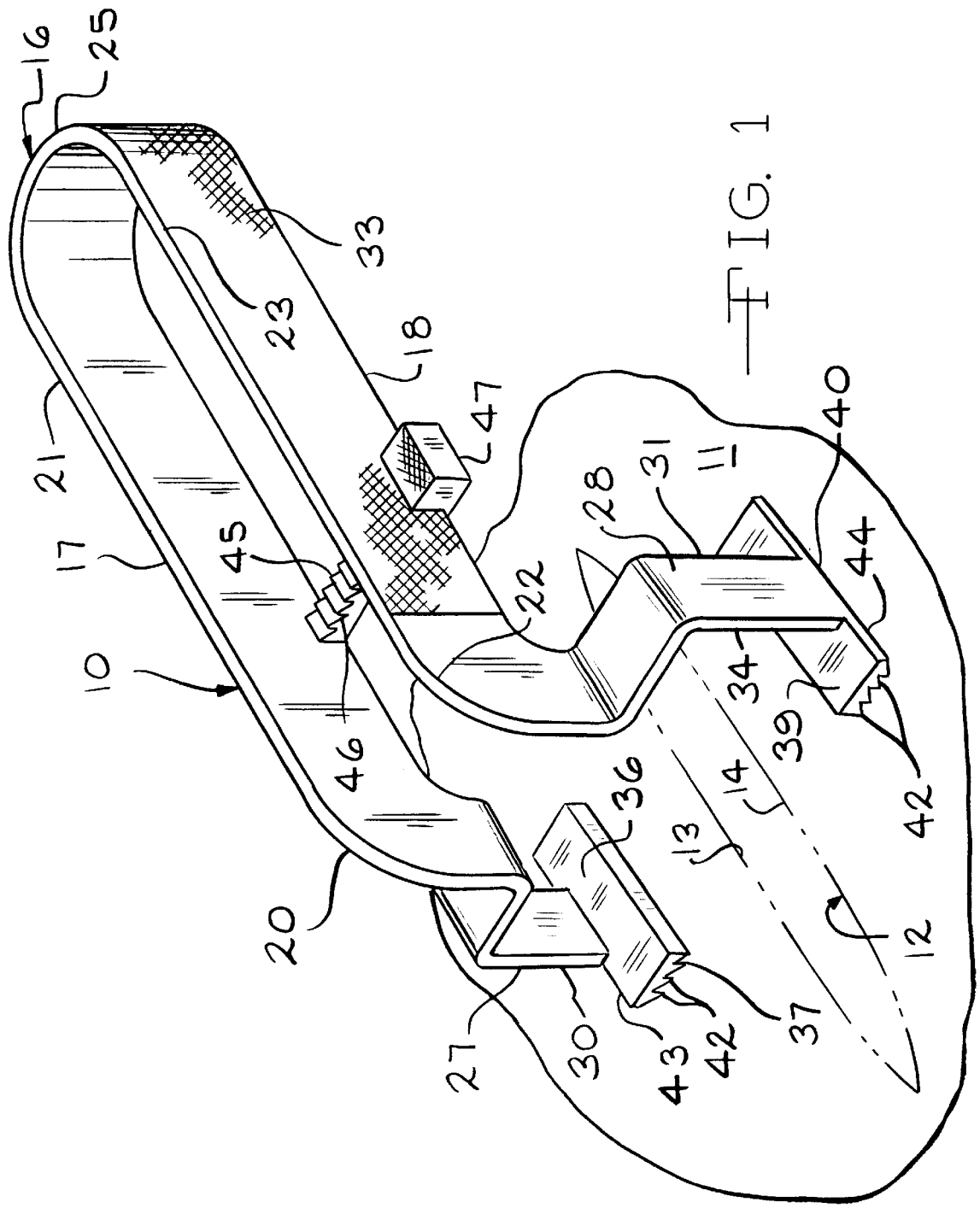
FIG. 1 is a perspective view of tissue approximation forceps, according to the present invention, in an uncompressed position.

Tissue approximation forceps, according to the present invention, are generally indicated in FIG. 1 by the reference number 10. A portion of a patent's skin surface is generally indicated by the reference number 11. A wound 12 having spaced edges 13 and 14 is also indicated.

When prior art forceps are used to approximate the edges of a wound, the forceps have surfaces which are parallel to one another. These forceps indent the skin as they close, while grabbing a portion of the skin. This results in the wound edges being everted or moved upwardly from the overall skin surface. This is desirable for suturing the wound because the edges eventually flatten and give an acceptable result.

However, as noted above, when a tissue glue is used to close a wound, everting the wound edges prior to closure is not desirable. The tissue approximation forceps 10, according to the present invention, are designed so they do not evert the wound edges 13 and 14 during approximation. The tissue approximation forceps 10 include a handle 16 having handle members 17 and 18. The handle member 17 has a first end 20 and a second end 21. Similarly, the handle member 18 has a first end 22 and a second end 23. An end member 25 joins together the second end 21 of the handle member 17 and the second end 23 of the handle member 18. A pair of leg members 27 and 28 extend outwardly from the first ends 20 and 22 of the pair of handle members 17 and 18. In the embodiment shown in FIGS. 1 and 2, the leg member 27 extends downwardly from the first end 20 of the handle member 17 and the leg member 28 extends downwardly from the first end 22 of the handle member 18. Preferably, the leg members 27 and 28 include offset portions 30 and 31, respectively. When the forceps 10 are moved to the closed position, shown in FIG. 2, the offset portions 30 and 31 provide a better access to the wound and a better viewing area as opposed to closed prior art forceps which tend to obscure the work area. A textured pattern, illustrated in FIG. 1 by the reference number 33 is preferably applied to the exterior surface of the handle members 17 and 18.

While the tissue approximation forceps 10 may be constructed of various materials including metal compositions, plastic is the preferred material. The tissue approximation forceps 10 are preferably constructed from a polyethylene material or a polypropylene material. When a tissue glue is used to close the wound edges 13 and 14, the polyethylene and polypropylene materials have a relatively low bondability to normally used tissue glues. When a plastic material is used to construct the tissue approximation forceps 10, the textured pattern 33 can be molded into the surfaces of the plastic handle members 17 and 18.

FIG. 1 illustrates the uncompressed position of the tissue approximation forceps 10. FIG. 2 illustrates the compressed position of the tissue approximation forceps 10. When in the compressed position, illustrated in FIG. 2, the offset portions 30 and 31 of the leg members 27 and 28 define an expanded gap 34 which allows application of the tissue glue to the approximated edges 13 and 14 of the wound 12 in an open and unrestricted fashion.

Referring to FIGS. 1, 2 and 3, a grip member 36 having a grip surface 37 is mounted at the lower end of the offset portion 30 of the leg member 27. Similarly, a grip member 39 having a grip surface 40 is mounted at the lower end of the offset portion 31 of the leg member 28.

Preferably, the grip members 36 and 39 extend inwardly from the offset portions 30 and 31 of the leg members 27 and 28. The offset portions 30 and 31 are connected at the outer edges 43 and 44 of the grip members 36 and 39. This gives the greatest viewing area when the forceps 10 are in the closed position, shown in FIG. 2. The gripping surfaces of prior art forceps move toward one another in engaging, parallel planes, such as the jaws of a vice. In the forceps 10, the grip surfaces 37 and 40 approach one another as they move between the uncompressed position and compressed position, shown in FIGS. 1 and 2. In this embodiment, the grip surfaces 37 and 40 lie in a common plane, rather than in parallel planes. The planes of the grip surfaces 37 and 40 do not engage one another upon closing. As shown in FIG. 3, the grip surfaces 37 and 40 include a plurality of parallel, longitudinally extending, generally V-shaped projections 42.

Referring to FIGS. 1 and 2, a locking arm 45 is integrally connected to the handle member 17 and defines a longitudinally extending ratchet 46 along its upper surface. While the locking arm 45 and its ratchet 46 are not always needed in tissue approximation forceps, they are advantageous when the forceps 10 are to be in the closed position for a period of time. A tab 47 is mounted at the other end of the locking arm 45. The handle member 18 defines a pawl opening 48. The pawl opening 48 receives one of the aligned teeth of the ratchet 46 to secure the tissue approximation forceps 10 in the clamped relationship shown in FIG. 2, after proper tissue approximation.

In operation, referring to FIGS. 1 and 2, the tissue approximation forceps 10 are moved into position adjacent the patient skin surface 11 with the gripping members 36 and 39 straddling the wound 12. The tissue approximation forceps 10 are in the uncompressed position shown in FIG. 1 at this time. The handle members 17 and 18 are then compressed. The gripping surfaces 37 and 40 engage the skin tissue on opposite sides of the wound 12. Further compression approximates the edges 13 and 14 without everting the edge surfaces of the skin tissue. The ratchet 46 of the locking arm 45 moves into a lock position with the aligned pawl opening 48. At this time, the physician may apply a tissue glue to the approximated wound 12. While the locking arm 45 is mounted on the lower side of the handle member 17, it can also be mounted on the upper side of the handle member 17 or on the handle member 18.

To release the locking arm 45, the tab 47 is pushed or pulled downwardly and the tissue approximation forceps 10 returned to the uncompressed position shown in FIG. 1.

Figures 4, 5:
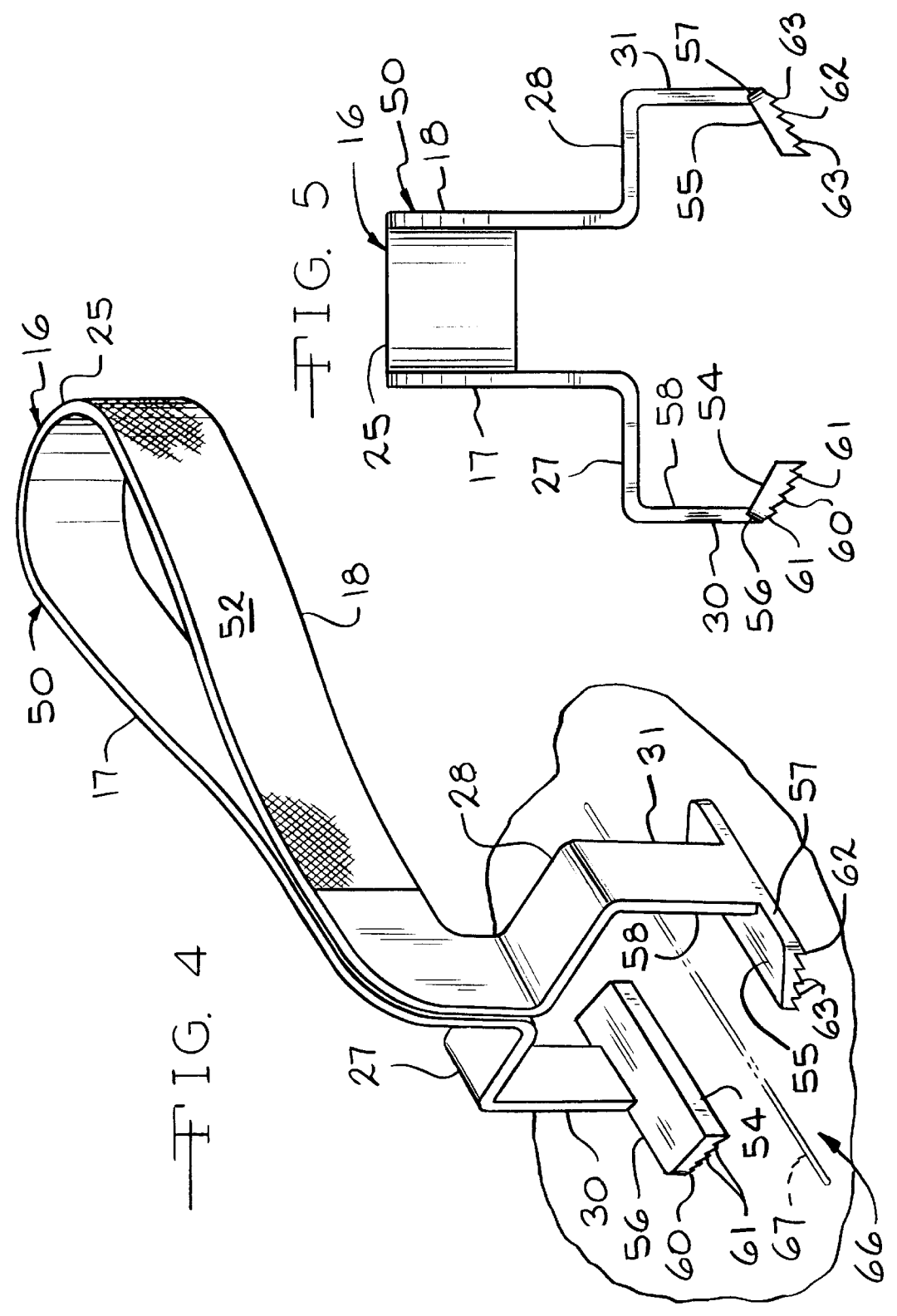

Another embodiment of tissue approximation forceps, according to the present invention, are generally indicated by the reference number 50 in FIGS. 4 and 5. The forceps 50 include a handle 16 having handle members 17 and 18. A pair of leg members 27 and 28 extend outwardly from the handle members 17 and 18. The leg members 27 and 28 include offset portions 30 and 31, respectively. A textured pattern 52 is applied to the exterior surface of the handle members 17 and 18. In the FIGS. 4 and 5 embodiment, inclined grip members 54 and 55 extend inwardly from the respective offset portions 30 and 31 of the leg members 27 and 28. The offset portions 30 and 31 are connected at edges 56 and 57 of the grip members 54 and 55 to define a large viewing area gap 58 when the tissue approximation forceps 50 are in the closed position as illustrated in FIG. 4. The inclined grip member 54 includes a grip surface 60 having sharp projections 61. Similarly, the inclined grip member 55 includes a grip surface 62 having a plurality of sharp projections 63.

When the tissue approximation forceps 50 are moved from the open position shown in FIG. 5 to the closed position shown in FIG. 4, the projections 61 and 63 are urged into against the skin 66. The inclined grip members 54 and 55 grip the skin 66 and approximate a wound 67 as the inclined grip members 54 and 55 are moved to the FIG. 4 closed position. As best shown in FIG. 5, the inclined grip members 54 and 55 and their grip surfaces 60 and 62 are located in intersecting planes as opposed to the prior art parallel plane structures, which are similar to the jaws of a vice.

The tissue approximation forceps 50 may be constructed of various materials including metal compositions. However, plastic is the preferred material. Preferred plastics are polyethylene materials and polypropylene materials.

In the tissue approximation forceps 50 a locking member, such as a rachet mechanism is not employed between the handle members 17 and 18 to temporarily secure the legs in their closed position.

Many revisions may be made to the above-described embodiments without departing from the scope of the invention or from the following claims.

We claim:

1. Tissue approximation forceps comprising a handle having a pair of handle members, each of said handle members having first and second ends, said second ends of said pair of handle members being joined together, a pair of leg members extending outwardly from said first ends of said pair of handle members and a grip member mounted by each of said leg members, each of said grip members having a grip surface, said grip surfaces lying in a common plane, each of said grip surfaces including a plurality of tissue gripping projections, whereby when said handle members are moved together, said grip members and said grip surfaces are moved toward each other to approximate the separated tissue, without everting the tissue edges.

2. Tissue approximation forceps, according to claim 1, wherein each said leg members includes an offset portion adjacent said grip members, said handle members being moveable between an uncompressed position and a compressed position, said offset portions of said leg members defining a gap when said leg members are in such compressed position.

3. Tissue approximation forceps, according to claim 1, wherein each of said grip members have a grip surface portion lying in a separate plane, said separate planes intersecting one another.

4. Tissue approximation forceps, according to claim 2, wherein each of said grip members has an outer edge, said offset portion being connected to said outer edge of said grip member, wherein said grip surfaces extending inwardly from said offset legs.

5. Tissue approximation forceps, according to claim 1, wherein said handle members include an inner surface and an outer surface, said handle members defining a textured pattern on their outer surfaces.

6. Tissue approximation forceps, according to claim 1, wherein said tissue approximation forceps are constructed of a metal composition.

7. Tissue approximation forceps, according to claim 1, wherein said tissue approximation forceps are constructed of a plastic material.

8. Tissue approximation forceps, according to claim 7, wherein said plastic material is a polyethylene material.

9. Tissue approximation forceps, according to claim 7, wherein said plastic material is a polypropylene material.

10. Tissue approximation forceps, according to claim 1, wherein said projections comprise a plurality of longitudinally extending, parallel projections, having generally V-shaped cross-sections.

11. Tissue approximation forceps, according to claim 1, including a locking arm extending between said handle members.

12. Tissue approximation forceps, according to claim 11, wherein said locking arm is connected to one of said handle members, said locking arm defining a ratchet for engaging the other one of said handle members.

13. Tissue approximation forceps comprising a handle having a pair of handle members, each of said handle members having first and second ends, said second ends of said pair of handle members being joined together, a pair of leg members extending outwardly from said first ends of said pair of handle members and a grip member mounted by each of said leg members, each of said grip members having a grip surface, said grip surfaces lying in a common plane, whereby when said handle members are moved together, said grip members and said grip surfaces are moved toward each other to approximate the separated tissue, without everting the tissue edges.

* * * * *